United States Patent [19]

Rabinovich et al.

[11] 4,288,347

[45] Sep. 8, 1981

[54] NOVEL CATALYST FOR DEALKYLATING ALKYL BENZENES AND FRACTIONS OF AROMATIZED BENZINES BY CONVERSION WITH STEAM

[76] Inventors: Georgy L. Rabinovich, ulitsa Antonova-Ovseenko, 19, korpus 2, kv. 104; Gdal N. Maslyansky, Moskovsky prospekt, 189, kv. 64; Ljubov M. Birjukova, Zhdanovskaya naberezhnaya, 9, kv. 2, all of Leningrad; Emmanuil A. Levitsky, ulitsa Akademicheskaya, 6, kv. 42, Novosibirsk; Kira L. Volkova, ulitsa Antonova-Ovseenko, 19, korpus 2, kv. 4, Leningrad; Zoya P. Lukina, Manezhny pereulok, 2, kv. 2, Leningrad; Viktor N. Mozhaiko, ulitsa Nevskaya, 3, kv. 3, Otradnoe Leningradskoi oblasti, all of U.S.S.R.

[21] Appl. No.: 49,722

[22] Filed: Jun. 18, 1979

[51] Int. Cl.$^3$ .................. B01J 27/02; B01J 23/14; B01J 23/16; B01J 23/62

[52] U.S. Cl. ................... 252/439; 252/464; 252/465; 252/466 PT; 252/466 B; 585/487

[58] Field of Search ......... 252/439, 464, 465, 466 PT, 252/466 B

[56] References Cited

U.S. PATENT DOCUMENTS

| | | | |
|---|---|---|---|
| 3,291,720 | 12/1966 | Dobres et al. | 252/439 X |
| 3,436,433 | 4/1969 | Lester | 585/487 |
| 3,436,434 | 4/1969 | Lester | 585/487 |
| 3,649,565 | 3/1972 | Wilhelm | 252/466 PT |
| 3,649,707 | 3/1972 | Lester | 585/487 |
| 3,840,389 | 10/1974 | Kobylinski et al. | 252/439 X |
| 4,053,389 | 10/1977 | Wilhelm | 252/466 PT X |
| 4,199,436 | 4/1980 | Courty | 208/124 |

*Primary Examiner*—Delbert E. Gantz
*Assistant Examiner*—William G. Wright
*Attorney, Agent, or Firm*—Lackenbach, Lilling & Siegel

[57] ABSTRACT

A catalyst for dealkylating alkyl benzenes and fractions of aromatized benzines by means of steam conversion is disclosed. The catalyst comprises rhodium or rhodium in a mixture with another noble metal from Group VIII of the Periodic System in an amount of 0.1 to 2 wt. % on a carrier of aluminum oxide and also at least one of the elements selected from the group consisting of sulfur, selenium or lead in an amount of 0.003 to 3 wt. %. To increase the yield of the final product, the catalyst also comprises at least one element selected from the group containing iron, cobalt, nickel, chrome, copper, and vanadium in an amount of 0.01 to 5 wt. %, and at least one of the elements of the alkaline or alkaline earth metals or mixtures thereof in an amount of 0.01 to 5 wt. %.

The proposed catalyst features a high degree of selectivity for dealkylating alkyl benzenes in combination with a high degree of starting feed conversion.

12 Claims, No Drawings

NOVEL CATALYST FOR DEALKYLATING ALKYL BENZENES AND FRACTIONS OF AROMATIZED BENZINES BY CONVERSION WITH STEAM

FIELD OF THE INVENTION

The present invention relates generally to the field of petrochemical synthesis, and more specifically, to a novel catalyst for dealkylating alkylbenzenes and fractions of aromatized benzines by conversion with aqueous steam.

The catalyst of the present invention is highly useful for the dealkylation of alkylbenzenes, primarily toluene and $C_9$-$C_{10}$ alkylaromatic hydrocarbons which are produced in the reforming of wide benzine fractions and hydrorefined pyrolysis benzines.

The catalyst of the present invention is particularly adapted for deriving low-molecular aromatic hydrocarbons, especially benzene.

BACKGROUND OF THE INVENTION

Benzene is known to be the most valuable aromatic hydrocarbon. It enjoys extensive application in the manufacture of a great variety of chemicals, such as cyclohexane, ethylbenzene, cumene, aniline, which in turn are utilized in the production of plastics, synthetic fibers, rubbers, dye-stuffs and the like.

Heretofore it was customary practice to obtain benzene mainly by catalytic reforming narrow benzine fractions on alumoplatinum catalysts. A substantial amount of benzene is also produced via dealkylation of toluene in the presence of hydrogen (hydrodealkylation) in accordance with the following reaction:

$$C_6H_5CH_3 + H_2 \rightarrow C_6H_6 + CH_4$$

Known in the prior art are catalysts for dealkylating alkylbenzenes in the presence of steam, comprising nickel as an active component (U.S. Pat. No. 3,634,532; FRG Pat. No. 2,049,151).

A major disadvantage inherent in the nickel catalysts disclosed therein is their extremely low stability. The interregeneration period of such catalysts is confined to a few hours.

Known in the prior art are catalysts of the platinum group metals deposited on an inert porous carrier, most frequently aluminum oxide (cf. USSR Inventor's Certificate No. 198,310; FRG Pat. No. 1,793,129; U.S. Pat. No. 3,595,932). Use is made of various modifications of aluminum oxide, such as $\gamma$-, $\eta$-, $\delta$-, $\theta$-, $\alpha$-forms, as well as alumosilicates. The stated catalysts are promoted by alkaline, alkaline earth metals, metals of the Fe subgroup (iron, cobalt, nickel), the V subgroup (vanadium, niobium, tantalum), the Cr subgroup (chromium, molybdenum, tungsten), copper and also by the additions of elements of the lanthanum and actinium groups (U.S. Pat. Nos. 3,436,433; 3,436,434; 3,649,706; 3,649,707; 3,848,014; British Pat. No. 1,313,941; Jap. Appl. No. 74-126,630).

The aforementioned prior art catalysts for steam dealkylation processes look more promising than the nickel-containing contacts insofar as stability is concerned.

A disadvantage of such catalysts lies in the appreciable specific gravity of secondary reactions involved in cleavage of the benzene ring, which tends to impair the selectivity of benzene formation and, as a consequence to decrease the yield of the final product.

Furthermore, an acceptable dealkylation selectivity level of about 90–95 mol.% of that theoretically feasible is attained with the foregoing catalysts only at a relatively low degree of feed conversion (40–60%).

A higher extent of starting feed conversion, e.g. by means of elevating the temperature, inevitably results in further reduction of the process selectivity and, hence, in an increase of costly hydrocarbon feed losses.

Among the platinum group metals, rhodium when applied to aluminum oxide has the highest activity (USSR Inventor's Certificate No. 198,310; FRG Pat. No. 1,793,124). The principal disadvantage of the alumorhodium catalyst is its low selectivity in the reaction of toluene demethylation amounting to 90 mol.% with 60% toluene conversion, which corresponds to 54 mol.% benzene yield.

Alkylaromatic hydrocarbons under the conditions prevalent in the steam dealkylation process, apart from the basic reaction of dealkylating into benzene, are apt to undergo complete decomposition to oxides of carbon and hydrogen, for instance:

$$C_6H_5CH_3 + (7+n)H_2O \rightarrow CO_2 + (7-n)CO + (11+n)H_2$$

Ratio of the product yield of a specific dealkylation reaction to the total conversion of hydrocarbon feed characterizes the selectivity of dealkylation, which for the given case of toluene demethylation can be expressed as follows:

$$\text{Selectivity, mol.\%} = \frac{\text{benzene yield, mol.\%}}{\text{toluene conversion, \%}} \cdot 100$$

The process selectivity is largely dependent on the properties of catalyst being used.

The catalysts, wherein besides rhodium, additions of other ingredients contributing to the increase of dealkylation selectivity, feature a higher level of selectivity.

Known in the prior art is a catalyst containing the following elements, in wt.%: 0.9% rhodium, 10% chromium oxide, 1% ferric oxide and 2% potassium oxide, the balance being aluminum oxide (U.S. Pat. No. 3,436,433). According to this patent the stated catalyst was employed in the reaction of toluene demethylation with steam.

A major disadvantage of this prior art catalyst is its relatively low selectivity in the specific reaction amounting to 94.9 mol.%. Another disadvantage is the fact that the aforesaid selectivity is achieved at inadequate toluene conversion per run (about 50%).

A higher degree of toluene conversion, as mentioned hereinabove, results in still more drastic reduction of demethylation selectivity, i.e. in decrease of the benzene yield per total amount of toluene reacted.

The promoting additions revealed in the patent do not ensure selectivity of toluene demethylation higher than 95 mol.% at a high degree of feed conversion (above 50%).

Despite the fact that the process of steam dealkylation has a number of obvious advantages, industrial techniques of such a process have not developed, inasmuch as a catalyst featuring the selectivity and stability sufficient for effecting the process on a commercial scale is not available in the present state of the art.

SUMMARY OF THE INVENTION

It is an object of the present invention to provide a catalyst for dealkylating alkyl benzenes and fractions of aromatized benzines, ensuring high selectivity in combination with a high degree of starting feed conversion.

With this object in mind, there is proposed a catalyst for dealkylating alkyl benzenes and fractions of aromatized benzines, comprising rhodium or rhodium in a mixture with another noble element from Group VIII of the Periodic System in an amount of 0.1 to 2.0 wt.%, deposited on a carrier, which catalyst according to the invention, further comprises at least one of the elements selected from the group consisting of sulfur, selenium, or lead in an amount of 0.003 to 3.0 wt.%.

It has been found by the authors that even the slightest amounts of sulfur (about 0.003 wt.%), which are occasionally present in aluminum oxide as impurities, lead to a substantial increase of the selectivity effect displayed by dealkylation catalysts. When introducing sulfur into the catalyst in greater amounts, an exclusively high level of selectivity can be attained (up to 100%). The process of dealkylation therewith should be conducted at higher temperatures.

The fact that sulfur can be utilized as a promotor for a dealkylation catalyst was surprising, since Japanese Pat. No. 7,486,326 describes sulfur as highly toxic and thorough treatment is required to remove sulfuric compounds from the source material.

The effects of selenium and lead are similar to that of sulfur and selectivity of the catalysts obtained therewith is as high as in the case of sulfur.

Preferably, the above catalyst comprises sulfur as selenium in an amount of 0.003-0.1 wt.%. Such catalyst may comprise lead instead of sulfur or selenium in an amount of 0.01-3% wt.%.

The effect of adding sulfur, selenium or lead to the catalysts comprising rhodium or rhodium in a mixture of another metal from Group VIII of the Periodic System carried on aluminum oxide, particularly to the alumina-rhodium catalyst, is still higher if these novel additions (sulfur, selenium, lead) are introduced into the catalyst composition together with such additions as iron, cobalt, nickel, chromium, copper, vanadium in an amount of 0.01-5 wt.%.

Moreover, to improve the stability and to reduce coke formation, the additions of alkaline and/or alkaline earth metals are introduced into the catalyst composition in an amount of 0.01-5 wt.%.

The most preferred catalyst compositions for dealkylating alkyl benzenes are as follows:
catalyst comprising (in wt.%):
  0.1-1 rhodium, 0.005-0.1 sulfur, 0.05-2 copper, 0.05-3 potassium, the balance being aluminum oxide;
catalyst comprising (in wt.%):
  0.1-1 rhodium, 0.005-0.1 sulfur, 0.1-3 iron, 0.05-3 potassium, the balance being aluminum oxide;
catalyst comprising (in wt.%):
  0.1-1 rhodium, 0.01-1 lead, 0.1-3 iron, 0.01-2 potassium, the balance being aluminum oxide;
catalyst comprising (in wt.%):
  0.1-1 rhodium, 0.01-1 lead, 0.05-2 copper, 0.01-2 potassium, the balance being aluminium oxide;
catalyst comprising (in wt.%):
  0.1-1.0 rhodium, 0.005-0.1 sulfur, 0.05-2 copper, 0.05-3 potassium, 0.05-0.3 magnesium, the balance being aluminum oxide;
catalyst comprising (in wt.%):
  0.1-1.0 rhodium, 0.005-0.1 sulfur, 0.1-3 iron, 0.05-3 potassium, 0.05-0.3 magnesium, the balance being aluminum oxide.

In the abovestated compositions sulfur can be completely or partially substituted by selenium.

The process of dealkylation with said catalysts is effected at a temperature of 400°-700° C., preferably 450°-650° C., at a pressure ranging from 1 to 30 gauge atm, preferably 1-15 gauge atm at a hydrocarbon source material volume rate in the range of 0.3-10 volumes per volume of catalyst per hour, preferably 1-3, and at a steam to hydrocarbon mole ratio of 2:20; preferably 3:10. Toluene, xylolenes, ethylbenzene, mixtures of $C_6$-$C_{10}$ aromatic hydrocarbons, fractions of reforming catalysts comprising, apart from aromatic hydrocarbons, nonaromatic ones, fractions of pyrolysis hydrorefined benzines comprising benzene, toluene, $C_8$-$C_9$ aromatic and nonaromatic hydrocarbons (paraffinic and naphthenic) are used as source materials.

The basic product prepared the proposed method of dealkylation is benzene, a by-product being a hydrogen-containing gas, which can be employed as fuel or for the purpose of producing hydrogen.

Use of $C_9$-$C_{10}$ aromatic hydrocarbons as starting material enables the production of benzene, toluene and xylolenes as basic products. Products which do not have any practical value, such as toluene, can be recycled in the process of dealkylation in order to step up the yield of more valuable products, e.g. benzene.

According to the invention, the catalyst carrier is aluminum oxide having a specific surface of 10-400 $m^2/g$ and a total porous volume, 0.3-1.2 $cm^3/g$.

The process of preparing the catalyst itself is not critical to achieving the intrinsic properties thereof and, thus, any of a variety of prior art methods is applicable.

The catalyst components are applied onto the carrier by impregnation either at a time or by means of sequential impregnations with aqueous or any other appropriate solutions of the aforesaid substances. The components can also be introduced into a paste of aluminum hydroxide with subsequent granulating and drying procedures.

The impregnation can be accomplished either by a solution volume equal to total volume of the carrier pores, or by an excess volume of the solution, with subsequent discharge of the solution excess or evaporation of the water excess.

As soluble metal salts, there may be used halide compounds, hydrocarbonates, nitrates, formates, acetates, oxalates, acids and ammonium salts thereof. However, when introducing metals into the composition of catalysts, sulfur-containing salts (sulfates, sulfites) should be either excluded or restricted, since in such a case sulfur together with a metallic cation into the catalyst may be in an amount which may prove to be excessive as compared to the optimum required for the catalyst.

Sulfur in strictly pre-assigned amounts can be introduced into the catalyst by impregnation with both aqueous solutions of acids (sulfuric, sulfurous, hyposulfurous, hydrosulfurous) or salts thereof, or by solutions of organic compounds (mercaptans, thioalcohols, thioethers, thiophene and the like).

It is more convenient to introduce sulfur with the help of compounds containing $SO_4$ and $SO_3$ groups. Selenium can be also introduced by impregnation with solutions of selenic, selenious acids or salts thereof. To introduce lead use is made of its soluble compounds, for example lead chlorides and acetates.

When applying the components onto aluminum oxide separately, between the impregnating stages, in addition to drying the catalyst at 100°–200° C., there may be performed calcination at a temperature of 300°–600° C. and/or reduction with hydrogen or a hydrogen-containing gas at a temperature of 250°–550° C. Upon application of the final component the catalyst is dried at 100°–200° C. and then calcinated in the flow of air or nitrogen at a temperature of 300°–600° C.

Prior to contact with alkyl aromatic hydrocarbons, the calcined catalyst is reduced with hydrogen or a hydrogen-containing gas at a temperature of 250°–550° C. to convert the metallic oxides resulting from the calcination into their reduced active forms.

The platinum group elements in the reduced catalyst are mainly in a metallic state. The alkaline and alkaline earth metals are in the form of oxides and are likely to form aluminum oxide compounds of the aluminate type. Iron, cobalt, nickel, chromium, vanadium, copper, and lead probably are present, partly in a reduced state, partly in an ionic form. Sulfur and selenium in the calcined catalyst are always in the form of sulfate and selenate ions, respectively, but in the reduced catalyst they can also be in the form of sulfides and selenides of metals.

The proposed catalyst features the following advantages over the prior art catalysts:

higher level of the dealkylation selectivity and, accordingly, higher yield of the ultimate products per feed reacted;

the possibility of effecting the process with higher feed conversion per run and with essentially no reduction of the process selectivity;

high stability.

For a better understanding of the present invention there are presented hereinbelow specific examples of the composition of the proposed catalyst.

EXAMPLE 1

Catalyst 1 is composed of (in wt.%):
0.6: rhodium
0.003: sulfur
carrier being the balance The above catalyst is produced as follows. 100 grams of a carrier calcined at 550° C. for 2 hours were impregnated with 120 ml of an aqueous solution containing 0.6 grams of rhodium in the form of the trihydrate of rhodium trichloride and 2.4 ml of glacial acetic acid. Excess water was evaporated at 50° C. under continuous stirring. After evaporation the catalyst was dried at 130° C. for 3 hours and calcined in a flow of air gradually increasing the temperature to 500° C. The calcination was maintained at 500° C. for 2 hours.

The carrier used was a commercial aluminum oxide in the form of spheres of 2.5 mm diameter. A specific surface area of the carrier—230 $m^2$/gr, a total porous volume—0.55 $cm^3$/gr. The carrier contained 0.003 wt.% sulfur (as an admixture).

This catalyst was tested in the reaction of toluene demethylation with aqueous steam. The test results are given in Table 1.

Toluene was chosen as a model hydrocarbon for testing the activity and selectivity of the catalysts since its dealkylation proceeds with the greatest difficulty and with a lower selectivity than the dealkylation of $C_8$–$C_{10}$ aromatic hydrocarbons.

The dealkylation of toluene with steam at atmospheric pressure was conducted a quartz reactor of 16 mm in diameter provided with a pocket for a thermocouple of 4 mm diameter 3.2 $cm^3$ of the calcined catalyst were charged into the reactor, reduced with hydrogen fed at a rate of 6 liters/hr with a gradual increase (for 3 hours) in temperature to 500° C. and held at this temperature for 2 hours. Upon termination of the reduction, water was fed to the reactor in an amount of 6 ml/hr, the hydrogen feed was turned off and a required testing temperature was set, whereafter toluene was fed at a rate of 6 ml/hr. The steam-gas mixture of the reaction products discharged from the reactor was periodically examined by the flow chromatography method.

The discharge of the products and nonreacted feed was performed every 6 hours, a hydrocarbon layer was isolated and an analysis of the gaseous and liquid products was carried out by gas chromatography.

The catalyst test results are given in Tables 1–5, wherein the test conditions are also indicated.

EXAMPLE 2

Catalyst 2 is composed of (in wt.%):
0.6: rhodium
0.001: sulfur
carrier being the balance The above catalyst is produced as follows. 100 grams of a carrier were impregnated with 120 ml of an aqueous solution containing 0.6 gr of rhodium in the form of rhodium trichloride trihydrate and 2.4 ml of glacial acetic acid. Further procedures are performed essentially as described in Example 1.

The carrier used was a γ-aluminum oxide of special purity as to the content of sulfur, in the form of extrudates of 1.5–2 mm in diameter and 3–5 mm in length. The physicochemical characteristics are close to those given in Example 1. The carrier contained sulfur in the form of an admixture in an amount of 0.001 wt.%.

The test results are given in Table 1.

EXAMPLE 3

Catalyst 3 is composed of (in wt.%):
0.6: rhodium
0.023: sulfur
carrier being the balance The above catalyst is produced as follows. 100 grams of the carrier described in Example 1 were impregnated with 60 ml of an aqueous solution containing 0.02 grams of sulfur in the form of ammonium sulfate, dried at 130° C. during 3 hours and impregnated with 120 ml of an aqueous solution containing 0.6 grams of rhodium in the form of the trihydrate of rhodium trichloride and 2.4 ml of glacial acetic acid. Further procedures were performed essentially as described in Example 1.

The testing results are given in Table 1.

EXAMPLE 4

Catalyst 4 is composed of (in wt.%):
0.6: rhodium
0.09: sulfur
carrier being the balance The method of preparing the above catalyst is similar to that described in Example 3, but into the first impregnating solution 0.09 grams of sulfur in the form of ammonium sulfate was introduced.

The results given in Table 1 testify to the fact that the addition of sulfur to the composition of the alumorhodium catalyst improves the selectivity of toluene demethylation. The temperature of Examples 3, 4 was chosen so as to provide 60-70% toluene conversion. An increase in the content of sulfur in the catalyst calls for an increased temperature of the process which is necessary to maintain a sufficiently high degree of feed conversion; however, temperature increase does not detrimentally affect the selectivity of demethylation.

EXAMPLE 5

Catalyst 5 is composed of (in wt.%):
0.55: rhodium
1.8: iron
0.003: sulfur
1.5: potassium
carrier being the balance The above catalyst is prepared as follows. 100 grams of the carrier of Example 1 were impregnated with 60 ml of an aqueous solution containing 0.57 grams of rhodium in the form of the rhodium trichloride trihydrate, 1.87 grams of iron in the form of the tetrahydrate of ferrous chloride, 1.56 grams of potassium in the form of potassium nitrate and 2.4 ml of glacial acetic acid. After holding for 24 hours the catalyst was dried at 50° C., 110° C. and 130° C. for 3 hours at each of the temperatures, then it was calcined in a flow of air at a temperature of 400° C. for 2 hours.

The catalyst test results of Examples 5-14 are given in Table 2.

Increased pressure tests were conducted in a steel tubular reactor of 36 mm diameter provided with a pocket for thermocouples of 8 mm in diameter. 60 cm$^3$ of calcined catalyst were charged into the reactor, reduced with hydrogen being fed at a rate of 100 liters/hr with a gradual temperature increase (for 8 hours) to 500° C. and held at this temperature for 2 hours. Upon termination of the reduction, water was fed to the reactor, the hydrogen feed was turned off and a required test temperature was set, whereafter toluene or reforming benzine was supplied to the reactor.

The liquid products of the reaction were condensed in a cooler, whereupon the gaseous products were separated from the liquid ones in a gas separator.

TABLE 1

Test conditions: Pressure: atmospheric
Toluene feed, space velocity: 1.8 hr$^{-1}$
Water-toluene mol. ratio: 6
Time: 3 hours

| Catalyst composition | Temperature, °C. | Toluene conversion, % | Benzene yield, mol. % | Demethylation selectivity, mol. % |
|---|---|---|---|---|
| Catalyst of Example 1 | 430 | 39.4 | 34.3 | 87.0 |
| | 460 | 56.3 | 47.1 | 83.7 |
| | 480 | 82.7 | 65.5 | 79.2 |
| Catalyst of Example 2 | 460 | 56.7 | 46.2 | 81.3 |
| Catalyst of Example 3 | 480 | 68.8 | 63.5 | 92.4 |
| Catalyst of Example 4 | 620 | 60.3 | 59.2 | 98.2 |
| | 650 | 83.2 | 79.4 | 95.4 |

EXAMPLE 6

Catalyst 6 is composed of (in wt.%):
0.55: rhodium
1.8: iron
1.5: potassium
0.008: sulfur
carrier being the balance The above catalyst is produced as follows. 100 grams of the carrier of Example 1 were impregnated with 60 ml of an aqueous solution containing 1.87 grams of iron in the form of the tetrahydrate of ferrous chloride and 0.005 grams of sulfur in the form of potassium sulfate. After holding the catalyst for 24 hours it was dried at 130° C. for 6 hours and calcined at 550° C. for 2 hours. After calcination the catalyst was impregnated with 120 ml of an aqueous solution containing 0.57 grams of rhodium in the form of rhodium trichloride trihydrate, 1.54 grams of potassium in the form of potassium nitrate and 4.8 ml of glacial acetic acid. The catalyst was allowed to stay for 24 hours, whereafter it was dried at 50° C., 110° C. and 130° C. for 3 hours at each of the temperatures and calcined in the flow of air at 400° C. for 2 hours. Tests were conducted in a manner similar to that described in Example 5.

The test results are given in Table 2.

EXAMPLE 7

Catalyst 7 is composed of (in wt.%):
0.6: rhodium
1.8: iron
1.0: potassium
0.2: magnesium
0.023: sulfur
the balance being carrier The above catalyst is produced as follows. 100 grams of the carrier of Example 1 were impregnated with 60 ml of an aqueous solution containing 0.02 grams of sulfur in the form of ammonium sulfate, dried for 3 hours at a temperature of 130° C. and then calcined in a flow of air at 550° C. for 2 hours. After calcination the catalyst was impregnated with 120 ml of an aqueous solution containing 0.62 grams of rhodium in the form of rhodium trichloride trihydrate, 1.86 of iron in the form of ferric nitrate nonahydrate, 1.03 grams of potassium in the form of potassium nitrate, 0.21 grams of magnesium in the form of magnesium nitrate and 4.8 ml of glacial acetic acid. After 3 hours of standing, excess water was evaporated under continuous stirring by a stream of air warmed to 50° C., then the catalyst was dried at 50° C., 110° C. and 130° C. for 3 hours at each of the temperatures and calcined in a flow of air at 400° C. for 2 hours. The catalyst was tested as described in Example 5.

The test results are given in Table 2.

EXAMPLE 8

Catalyst 8 is composed of (in wt.%):
0.6: rhodium
0.1: palladium
1.84: iron
0.3: nickel
1.0: potassium
0.2: magnesium
0.023: sulfur
the balance being carrier The above catalyst is produced essentially as described in Example 7, but into the second impregnating solution were additionally introduced 0.31 grams of nickel in the form of nickel nitrate hexahydrate and 0.1 grams of palladium in the form of palladium dichloride. The catalyst was tested in a manner similar to that described in Example 5.

The test results are given in Table 2.

EXAMPLE 9

Catalyst 9 is composed of (in wt.%):

0.6: rhodium
0.1: platinum
1.8: iron
0.4: cobalt
1.0: potassium
0.2: magnesium
0.023: sulfur
the balance being carrier The above catalyst is produced essentially as described in Example 7, but into the second impregnating solution were additionally introduced 0.42 grams of cobalt in the form of cobalt nitrate hexahydrate and 0.1 grams of platinum in the form of tetrachloroplatinic acid. Tests were carried out as in Example 5.

The test results are given in Table 2.

EXAMPLE 10

Catalyst 10 is composed of (in wt.%):
0.6: rhodium
1.0: vanadium
0.03: potassium
0.03: selenium
the balance being carrier The above catalyst is produced as follows 400 grams of aluminum hydroxide (the content of aluminum oxide is 25 wt.%) were mixed sequentially with 100 ml of an ammonium vanadate solution containing 1.02 grams of vanadium and 10 ml of ammonium selenite solution containing 0.03 grams of selenium. The mixture was thoroughly agitated, extruded, dried for 3 hours at 100° C. and then calcined in a flow of air at a temperature of 550° C. for 2 hours. Extrudates 1.5-2 mm diameter and 3-4 mm long were obtained. The resulting carrier was impregnated with 120 ml of an aqueous solution containing 0.62 grams of rhodium in the form of rhodium trichloride trihydrate, 0.03 grams of potassium in the form of potassium nitrate, and 4.8 ml of glacial acetic acid. Further procedures were performed essentially as described in Example 1. The catalyst was tested as in Example 5.

The test results are given in Table 2.

EXAMPLE 11

Catalyst 11 is composed of (in wt.%):
0.6: rhodium
3.0: chrome
1.5: potassium
0.03: sulfur
the balance being carrier The above catalyst is produced as follows. 100 grams of the carrier of Example 1 were impregnated with 120 ml of an aqueous solution containing 0.63 grams of rhodium in the form of rhodium trichloride trihydrate, 3.1 grams of chromium in the form of chromium trioxide, 1.57 grams of potassium in the form of potassium nitrate, 0.03 grams of sulfur in the form of ammonium sulfate, and 4.8 ml of glacial acetic acid. Further procedures were performed essentially as described in Example 1. The catalyst was tested as in Example 5.

The test results are given in Table 2.

EXAMPLE 12

Catalyst 12 is composed of (in wt.%):
0.6: rhodium
0.2: copper
2.3: potassium
0.003: sulfur (as an admixture)
the balance being carrier The above catalyst is produced as follows.

The carrier of Example 1 was used to prepare the catalyst.

100 grams of the carrier were impregnated with 120 ml of an aqueous solution containing 0.62 grams of rhodium in the form of rhodium trichloride trihydrate 0.21 grams of copper in the form of copper chloride, 2.36 grams of potassium in the form of potassium nitrate and 7.2 ml of hydrochloric acid (specific weight 1.19). Further procedures were performed essentially as described in Example 5. The catalyst was tested as in Example 5.

The test results are given in Table 2.

EXAMPLE 13

Catalyst 13 is composed of (in wt.%):
0.6: rhodium
0.018: sulfur
0.2: copper
2.5: potassium
the balance being carrier The above catalyst is produced as follows. 100 grams of the carrier of Example 1, calcined at 550° C. for 2 hours, were impregnated with 60 ml of an aqueous solution containing 0.015 grams of sulfur in the form of potassium sulfate. After keeping for 3 hours, excess moisture was removed by a stream of air heated to 50° C., then the catalyst was dried at 130° C. for 6 hours and calcined at 550° C. for 2 hours. After calcination the catalyst was impregnated with 120 ml of an aqueous solution containing 0.62 grams of rhodium in the form of rhodium trichloride trihydrate, 0.21 grams of copper in the form of copper chloride, 2.57 grams of potassium in the form of potassium nitrate, and 7.2 grams of hydrochloric acid (spec. weight=1.19). The catalyst was allowed to stand for 3 hours, excess water was evaporated by a stream of air heated to 50° C. to an air-dry state. After the evaporation the catalyst was dried at 50° C., 110° C. and 130° C. for 3 hours at each of the temperatures, calcined in the flow of air for 2 hours at 400° C. The catalyst was tested as in Example 5.

The test results are given in Table 2.

EXAMPLE 14

Catalyst 14 is composed of (in wt.%):
0.6: rhodium
0.03: selenium
0.2: copper
2.5: potassium
the balance being carrier The above catalyst is produced essentially as described in Example 13, but instead of sulfur 0.03 grams of selenium was introduced into the catalyst in the form of selenic acid. The sequence of the impregnating, drying and calcining operations is exactly the same as in Example 13. The catalyst was tested as in Example 5.

The test results are given in Table 2.

Table 2 contains the results of the foregoing tests which show the effectiveness of adding sulfur or selenium to the catalysts, comprising, in addition to rhodium and the above-stated elements, iron, cobalt, nickel, copper chromium, vanadium, as well as platinum, palladium, potassium and magnesium. The catalysts of Examples 5 and 12 do not comprise sulfur and are given as comparative.

TABLE 2

Pressure: 7 atm

| Catalyst No. | Water-toluene molar ratio | Space velocity of toluene hr$^{-1}$ | Catalyst test duration under given conditions, h | Temperature, °C. | Toluene conversion, % | Benzene Yield, mol. % | Demethylation selectivity, % | Gas composition, vol. % | | | | |
|---|---|---|---|---|---|---|---|---|---|---|---|---|
| | | | | | | | | H$_2$ | CO$_2$ | CO | CH$_4$ | C$_2$ |
| 5 | 6 | 1 | 250 | 455 | 63.8 | 59.0 | 92.5 | 54.9 | 25.3 | 1.3 | 17.9 | 0.6 |
| 6 | 6 | 1 | 250 | 455 | 64.0 | 61.5 | 96.1 | 61.3 | 23.9 | 1.0 | 13.4 | 0.4 |
| 7 | 6 | 1.3 | 24 | 430 | 39.8 | 39.0 | 98.0 | 73.9 | 20.5 | 0.4 | 4.7 | 0.5 |
| 7 | 3 | 2.6 | 180 | 500 | 52.3 | 51.7 | 98.7 | 60.9 | 23.8 | 1.8 | 12.6 | 0.9 |
| 8 | 6 | 2.6 | 180 | 485 | 58.5 | 57.8 | 98.9 | 63.3 | 19.9 | 2.2 | 14.2 | 0.4 |
| 9 | 6 | 2.6 | 180 | 490 | 63.1 | 61.7 | 97.8 | 65.2 | 21.3 | 1.7 | 11.4 | 0.4 |
| 10 | 6 | 1.3 | 180 | 485 | 70.4 | 68.5 | 97.5 | 66.7 | 21.0 | 2.3 | 9.4 | 0.6 |
| 11 | 6 | 1.3 | 180 | 485 | 71.2 | 69.5 | 97.6 | 62.1 | 20.0 | 1.7 | 15.4 | 0.8 |
| 12 | 3 | 2.6 | 120 | 520 | 70.0 | 62.8 | 89.6 | 39.4 | 35.4 | 4.3 | 20.8 | 0.1 |
| 13 | 3 | 2.6 | 120 | 520 | 65.0 | 63.1 | 97.0 | 58.2 | 28.1 | 1.2 | 12.3 | 0.2 |
| 14 | 3 | 2.6 | 120 | 525 | 66.7 | 65.9 | 98.8 | 56.3 | 27.2 | 1.7 | 14.6 | 0.2 |

EXAMPLE 15 (comparative)

Catalyst 15 is composed of (in wt.%):
0.6: rhodium
the balance being carrier

The above catalyst is produced as follows. The carrier was a spherical aluminum oxide (pellets' diameter is 2–2.5 mm). The specific surface of the carrier is 70 m$^2$/g the total volume of pores, 0.45 cm$^3$/g. The carrier contained as admixtures: 0.02 wt.% of sodium and 0.003 wt.% sulfur.

The above catalyst is produced essentially as described in Example 1.

The test results are given in Table 3.

EXAMPLE 16

Catalyst 16 is composed of (in wt.%):
0.6: rhodium
0.02: lead
the balance being carrier The carrier was aluminum oxide of Example 15.

The above catalyst is produced essentially as described in Example 1, but into the impregnating solution was additionally introduced 0.02 grams of lead in the form of lead acetate.

The test results are given in Table 3.

EXAMPLE 17

Catalyst 17 is composed of (in wt.%):
0.6: rhodium
0.2: lead
the balance being carrier The carrier was aluminum oxide as in Example 15.

The above catalyst is produced essentially as described in Example 16, the amount of lead introduced is 0.2 grams.

The test results are given in Table 3.

EXAMPLE 18

Catalyst 18 is composed of (in wt.%):
0.6: rhodium
0.5: lead
the balance being carrier The carrier was aluminum oxide as in Example 15.

The above catalyst is produced essentially as described in Example 16, the amount of lead introduced is 0.5 grams.

The test results are given in Table 3.

EXAMPLE 19

Catalyst 19 is composed of (in wt.%):
0.59: rhodium
1.0: lead
the balance being carrier The carrier was aluminum oxide as in Example 15.

The above catalyst is produced essentially as described in Example 16, the amount of lead introduced is 1.0 grams.

The test results are given in Table 3.

EXAMPLE 20

Catalyst 20 is composed of (in wt.%):
0.58: rhodium
3.0: lead
the balance being carrier The carrier was aluminum oxide as in Example 15.

The above catalyst is produced essentially as described in Example 16, the amount of lead introduced is 3.0 grams.

The test results are given in Table 3.

In Table 3 is shown the effect of adding lead to the rhodium-alumina catalyst on its activity and selectivity in the reaction of toluene demethylation.

The catalyst of Example 15 does not comprise lead, is given for the sake of comparison and lies beyond the scope of the present invention.

As in the case of the sulfur-containing catalysts, an increase in the content of lead improves the selectivity of demethylation; at the same time an increase in the process temperature is required.

EXAMPLE 21

Catalyst 21 is composed of (in wt.%):
0.6: rhodium
0.4: lead
0.9: iron
the balance being carrier The above catalyst is produced as follows. 100 grams of the carrier of Example 15 were impregnated with 120 ml of an aqueous solution containing 0.61 of rhodium in the form of rhodium trichloride trihydrate, 0.41 grams of lead in the form of lead acetate, 2.4 ml of glacial acetic acid and 0.92 grams of iron in the form of ferric nitrate nonahydrate. Excess water was evaporated at 50° C. under continuous stirring. After evaporation the catalyst was dried at 130° C. for 3 hours and calcined in a flow of air with a gradual temperature increase to 500° C. The calcination was continued at 500° C. for 2 hours.

The test results are given in Table 4.

TABLE 3

Test conditions: atmospheric: space velocity of toluene feed, 1.8 hr$^{-1}$; water-toluene mol. ratio: 6 time, 3 hours

| Catalyst No. | Temperature, °C. | Toluene conversion, % | Benzene yield, mol. % | Demethylation selectivity, mol. % |
| --- | --- | --- | --- | --- |
| 15 | 430 | 40.1 | 34.0 | 85.0 |
|  | 460 | 55.8 | 46.0 | 82.2 |
|  | 480 | 80.9 | 62.6 | 77.3 |
| 16 | 480 | 81.0 | 64.0 | 79.0 |
| 17 | 480 | 78.9 | 69.5 | 88.0 |
| 18 | 500 | 70.7 | 67.7 | 95.7 |
| 19 | 550 | 69.6 | 66.8 | 96.0 |
| 20 | 680 | 52.0 | 50.0 | 96.2 |

EXAMPLE 22

Catalyst 22 is composed of (in wt.%):
0.6: rhodium
0.4: lead
0.9: cobalt
the balance being carrier The above catalyst is produced essentially as described in Example 21, but instead of an iron salt 0.92 grams of cobalt were introduced into the impregnating solution in the form of cobalt nitrate hexahydrate.

The test results are given in Table 4.

EXAMPLE 23

Catalyst 23 is composed of (in wt.%):
0.6: rhodium
0.4: lead
0.9: nickel
the balance being carrier The above catalyst is produced essentially as described in Example 21, but instead of iron salt, 0.92 gr of nickel were introduced into the impregnating solution in the form of nickel nitrate hexahydrate.

The test results are given in Table 4.

EXAMPLE 24

Catalyst 24 is composed of (in wt.%):
0.6: rhodium
0.4: lead
3.0: chromium
the balance being carrier The above catalyst is produced essentially as described in Example 21, but instead of an iron salt, 3.1 grams of chromium were introduced into the impregnating solution in the form of chromium trioxide.

The test results are given in Table 4.

EXAMPLE 25

Catalyst 25 is composed of (in wt.%):
0.6: ruthenium
0.2: rhodium
the balance being carrier The above catalyst is produced as follows. 100 grams of the carrier of Example 15 were impregnated with 120 ml of an aqueous solution containing 0.6 grams of ruthenium in the form of ruthenium hydroxochloride, 0.2 grams of rhodium in the form of rhodium trichloride trihydrate and 7.2 grams of hydrochloric acid (spec. weight=1.19). After holding for 24 hours, excess solution was decanted, while the catalyst was dried and calcined as described in Example 1.

The test results are given in Table 4.

EXAMPLE 26

Catalyst 26 is composed of (in wt.%):
0.6: ruthenium
0.2: rhodium
0.3: lead
the balance being carrier The above catalyst is produced essentially as described in Example 25, but 0.3 grams of lead were introduced additionally into the impregnating solution in the form of lead acetate.

The test results are given in Table 4.

TABLE 4

Test conditions: Pressure, atmospheric; Space velocity of toluene feed, 1.8 hr$^{-1}$; Water-toluene mol. ratio, 6; time, 3 hours

| Catalyst No. | Temperature, °C. | Toluene conversion, % | Benzene yield, mol. % | Demethylation selectivity, mol. % |
| --- | --- | --- | --- | --- |
| 18 | 500 | 70.7 | 67.7 | 95.7 |
| 21 | 540 | 89.6 | 87.5 | 97.6 |
| 22 | 520 | 79.3 | 75.9 | 95.7 |
| 23 | 500 | 80.2 | 77.0 | 96.0 |
| 24 | 510 | 83.1 | 81.3 | 97.8 |
| 25 | 460 | 60.9 | 43.4 | 71.3 |
| 26 | 500 | 61.1 | 57.6 | 94.3 |

In Table 4 is shown the joint effect of lead and one of the elements selected from the group consisting of iron, cobalt, nickel, chromium.

With 80-90% toluene conversion, the selectivity of demethylation remains high, amounting to more than 97 mol.% (Examples 21, 24).

EXAMPLE 27

Catalyst 27 is composed of (in wt.%):
0.6: rhodium
0.3: copper
1.0: potassium
0.2: magnesium
the balance being carrier The above catalyst is produced as follows. 100 grams of the carrier of Example 1 were impregnated with 120 ml of an aqueous solution containing 0.61 grams of rhodium in the form of rhodium trichloride trihydrate 0.31 grams of copper in the form of copper chloride, 1.0 grams of potassium in the form of potassium nitrate, 0.22 grams of magnesium in the form of magnesium nitrate, and 4.8 ml of glacial acetic acid. Excess water was evaporated by a steam of air heated to 50° C. The catalyst was dried at 50° C., 110° C. and 130° C. for 3 hours at each of the temperatures and calcined in a flow of air at a temperature of 400° C. for 2 hours.

The test results are given in Table 5.

EXAMPLE 28

Catalyst 28 is composed of (in wt.%):
0.6: rhodium
0.3: copper
0.2: lead
1.0: potassium
0.2: magnesium
the balance being carrier The catalyst is produced essentially as described in Example 27, but 0.2 of lead was additionally introduced into the impregnating solution in the form of lead acetate.

The test results are given in Table 5.

In Table 5 it is shown that the use of a lead+copper combination in the composition of the catalyst enables one to attain 100% selectivity of the process together with a sufficiently high degree of toluene conversion.

The content of hydrogen in the gas when operating on such catalyst is more than 20 abs.% higher than while operating on a catalyst which does not comprise lead.

EXAMPLE 29

Catalyst 29 is composed of (in wt.%):
0.5: rhodium
0.3: copper
0.14: lead
the balance being aluminum oxide as the carrier As a material for dealkylation use is made of a fraction of reforming catalyzate boiling out within 105°–200° C. The composition of the feed in wt.%: 12.3—paraffinic hydrocarbons, 20.2—toluene, 33.6—aromatic $C_8$ hydrocarbons, 33.9—$C_9$-$C_{10}$ aromatic hydrocarbons. The test temperature, 500° C.; pressure, 7 atm. Space velocity of the hydrocarbon feed, 1.3 hr$^{-1}$; water/feed weight ratio, 2. Under these conditions the yield of the liquid product is 77 wt.%.

The composition of the liquid product (in wt.%):
1.2: paraffinic hydrocarbons
34.6: benzene
33.8: toluene
21.6: xylenes
8.8: $C_9$-$C_{10}$ aromatic hydrocarbons The composition of the gaseous products (in vol.%):
63.5: $H_2$
21.0: $CO_2$
1.7: CO
13.8: $CH_4$

EXAMPLE 30

Catalyst 30 is composed of (in wt.%):
0.7: rhodium
0.5: cesium
1.0: iron
0.02: sulfur
0.005: selenium
0.05: lead
the balance being aluminum oxide The above catalyst is produced as follows. 400 grams of aluminum hydroxide (the content of aluminum oxide, 25 wt.%) were mixed sequentially with 40 ml of a solution of lead dichloride taken in an amount of 0.05 grams as calculated for lead, 10 ml of a solution of sulfuric acid taken in an amount of 0.02 gr as calculated for sulfur, with 10 ml of a solution of selenic acid taken in an amount of 0.005 grams as calculated for selenium. After agitating the mixture was extruded, dried for 3 hours at 100° C. and calcined in a flow of air at a temperature of 600° C. for 2 hours. Extrudates 1.5–2 mm diameter and 3–4 mm length were obtained. The resulting carrier was impregnated with 110 ml of a solution containing 0.7 grams of rhodium in the form of rhodium trichloride trihydrate, 1.0 grams of iron in the form of iron dichloride tetrahydrate, 0.5 grams of cesium in the form of cesium nitrate and 2% of hydrochloric acid. The mixture was agitated and dried at 50°–60° C., then the catalyst was calcined in a flow of air, raising the temperature at a rate of 50° C. per hour to 450° C. and maintaining the catalyst at that temperature for 1 hour.

The catalyst was reduced in a flow of hydrogen at a temperature of 500° C. for 2 hours.

The testing of the catalyst was carried out in the demethylation of toluene with steam at a temperature of 480° C.; pressure, 5 atm; toluene feed space velocity, 1.3 hr$^{-1}$; toluene-water molar ratio, 6. The duration of the test was 24 hours. Toluene conversion, 74.8%, benzene yield, 73.8 mol.%. Dealkylation selectivity, 98.6 mol.%.

TABLE 5

Test conditions: Space velocity of toluene feed, 1.3 hr$^{-1}$; water-toluene mol. ratio, 6; catalyst charge, 60 cm$^3$; single test duration, 200 hours

| Catalyst No. | Pressure, atm | Temperature, °C. | Toluene conversion, % | Benzene yield, mol. % | Demethylation selectivity, mol. % | Gas composition, vol. % | | | | |
|---|---|---|---|---|---|---|---|---|---|---|
| | | | | | | $H_2$ | $CO_2$ | CO | $CH_4$ | $C_2$ |
| 27 | 7 | 470 | 69.6 | 64.1 | 92.2 | 46.2 | 26.0 | 0.7 | 26.2 | 0.9 |
| | 15 | 470 | 71.2 | 63.9 | 89.8 | 36.3 | 24.2 | 3.2 | 34.2 | 2.1 |
| 28 | 3 | 500 | 65.7 | 65.7 | 100 | 68.2 | 10.7 | 1.6 | 19.3 | 0.2 |
| | 7 | 500 | 67.5 | 67.5 | 100 | 65.5 | 10.5 | 1.3 | 22.5 | 0.3 |
| | 15 | 500 | 66.7 | 65.3 | 97.9 | 60.7 | 11.3 | 1.0 | 26.4 | 0.6 |

What is claimed is:

1. A catalyst for dealkylating alkyl benzenes and fractions of aromatized benzines by means of conversion with steam, consisting essentially of elements selected from the group consisting of rhodium or rhodium mixed with another metal from Group VIII of the Periodic Table in an amount of 0.01 to 5 wt.%; and at least one element selected from the group consisting of sulfur, selenium and lead in an amount of 0.003 to 3 wt.%; and at least one element selected from the group consisting of chromium, copper, and vanadium in an amount of 0.01 to 5 wt.%; and a carrier.

2. A catalyst as recited in claim 1, wherein sulfur is included in an amount of 0.003 to 0.1 wt.%.

3. A catalyst as recited in claim 1, wherein selenium is included in an amount of 0.003 to 0.1 wt.%.

4. A catalyst as recited in claim 1, wherein lead is included in an amount of 0.01 to 3 wt.%.

5. A catalyst as recited in claim 1, further including at least one element selected from the group consisting of alkaline metals, alkaline earth metals and mixtures thereof in an amount of 0.01 to 5 wt.%.

6. A catalyst as recited in claim 5, which comprises the following components (in wt.%):
rhodium: 0.1 to 1.0
sulfur: 0.005 to 0.1
copper: 0.05 to 2.0
potassium: 0.05 to 3.0 the balance being aluminum oxide

7. A catalyst as recited in claim 5, which comprises the following components (in wt.%):
rhodium: 0.1 to 1.0
sulfur: 0.005 to 0.1
iron: 0.1 to 3.0
potassium: 0.05 to 3.0
the balance being aluminum oxide 8. A catalyst as recited in claim 1, which comprises the following components (in wt.%):
rhodium: 0.1 to 1.0
lead: 0.01 to 1.0
iron: 0.1 to 3.0
potassium: 0.01 to 2.0
the balance being aluminum oxide 9. A catalyst as recited in claim 1, which comprises the following components (in wt.%):
rhodium: 0.1 to 1.0
lead: 0.01 to 1.0
copper: 0.05 to 2.0
potassium: 0.01 to 2.0
the balance being aluminum oxide 10. A catalyst as recited in claim 5, which comprises the following components (in wt.%):
rhodium: 0.1 to 1.0
sulfur: 0.005 to 0.1
copper: 0.05 to 2.0
potassium: 0.05 to 3.0
magnesium: 0.05 to 0.3
the balance being aluminum oxide 11. A catalyst as recited in claim 1, which comprises the following components (in wt.%):
rhodium: 0.1 to 1.0
sulfur: 0.005 to 0.1
iron: 0.1 to 3.0
potassium: 0.05 to 3.0
magnesium: 0.05 to 0.3
the balance being aluminum oxide 12. A catalyst as recited in claim 1, wherein the Group VIII elements vary from 0.1 to 2 wt.%.

* * * * *